United States Patent [19]

Bagaria et al.

[11] Patent Number: 5,023,108

[45] Date of Patent: Jun. 11, 1991

[54] AQUEOUS DISPERSIONS OF WAXES AND LIPIDS FOR PHARMACEUTICAL COATING

[75] Inventors: Suresh C. Bagaria, Somerset; Nicholas G. Lordi, Bloomfield, both of N.J.

[73] Assignee: Research Corporation, New York, N.Y.

[21] Appl. No.: 94,164

[22] Filed: Sep. 8, 1987

Related U.S. Application Data

[63] Continuation of Ser. No. 818,455, Jan. 13, 1986, abandoned.

[51] Int. Cl.$^5$ .............................................. A61K 9/42
[52] U.S. Cl. ........................................ 427/3; 424/476; 424/450
[58] Field of Search ................... 424/476, 450; 427/3

[56] References Cited

U.S. PATENT DOCUMENTS

| | | | |
|---|---|---|---|
| 2,800,463 | 7/1957 | Morrison | 427/213 |
| 3,438,797 | 4/1969 | Biddl | 424/476 |
| 3,644,130 | 2/1972 | Evans | 106/271 |
| 3,935,326 | 1/1976 | Groppenbachu | 427/3 |
| 3,981,957 | 9/1976 | Brederode | 264/13 |
| 4,002,706 | 1/1977 | Pretorious | 264/13 |
| 4,508,703 | 4/1985 | Redziniak | 424/38 |

Primary Examiner—Sam Silverberg
Attorney, Agent, or Firm—Scully, Scott, Murphy & Presser

[57] ABSTRACT

This invention relates to the coating of pharmaceutically useful solids with an emulsion comprising a wax/lipid, an emulsifying agent and water, which emulsion can be spray dried to form a powder which can subsequently be dispersed in water and coated onto the surface of medicaments to form a protective, enteric and/or controlled release of drug-containing granules, pellets and tablets.

12 Claims, No Drawings

AQUEOUS DISPERSIONS OF WAXES AND LIPIDS FOR PHARMACEUTICAL COATING

This is a continuation of copending application Ser. No. 818,455, filed on Jan. 13, 1986, now abandoned.

This invention relates to aqueous dispersions of waxes and lipids for pharmaceutical coating and more particularly is concerned with the preparation of an aqueous system for the coating of pharmaceutical solids, i.e. medicaments and the like, with waxes or lipids alone or in combination.

BACKGROUND OF THE INVENTION

The techniques employed for the application of wax and lipid coatings on solid dosage forms include the hot-melt application whereby the waxes and lipids are melted with an oil-soluble emulsifying agent and are applied to tablets or granules rotating in a coating pan.

Another method in use employs organic solvent solutions of waxy materials in which the waxes and lipids are dissolved in a suitable organic solvent such as chloroform and the organic solution is then applied on tablets or pellets in a conventional coating pan, for example.

Spray congealing is also in use and presents the advantage of producing directly a free flowing powder by spraying a suspension of finely-divided powdered medicament, molten wax and lipid into solid particulate form.

Aqueous film coating has gained use recently. A typical process involves dispersing a finely-divided powder of hydroxypropylmethylcellulose phthalate in an aqueous medium containing triacetin to give an aqueous coating liquid, spraying the coating onto the surface of a solid dosage form and thereafter drying the thus coated solid dosage form to provide an enteric coating.

None of these processes have been completely satisfactory. Organic coating liquids are undesirable as the use of large amounts of organic solvents involves problems of explosion or fire hazard as well as possible toxic effects and environmental pollution. The hot-melt and spray congealing methods involve the use of special equipment which is costly.

The use of aqueous polymer solutions for film coating purposes is limited to relatively low solids contents since the viscosity of such solutions rises sharply with an increase in concentration or molecular weight of the polymer. As a consequence of this relatively low polymer concentration, a number of separate layers of polymer must be built up in order to obtain a coating of adequate thickness for surface protection. This, in addition to the slow rate of evaporation of water and relatively large amounts of water to be removed, may result in a very long processing time. Furthermore, water sensitive drugs are prone to hydrolysis due to the long exposure of the drugs to water and many tablets must be sealed with water barriers such as shellac coatings prior to aqueous film coating.

It is an object of the present invention to provide a novel aqueous coating system which has none of the problems associated with the methods currently in use by the pharmaceutical industry.

It is a further object of the present invention to provide a novel aqueous coating system which can be used in current coating equipment without requiring the use of special expensive equipment or volatile solvents as in the case of the prior art methods presently in use.

BRIEF SUMMARY OF THE INVENTION

The present invention involves a novel formulation and process for converting waxes and lipids used for pharmaceutical and food coating encapsulation into a solid powder which can be reconstituted with water into an aqueous coating system for application as a protective, enteric and/or controlled release coating of drug-containing granules, pellets and tablets. The aqueous dispersion method of the present invention can be used to coat heat-sensitive materials as the product is not exposed to excessively high temperatures. The present emulsion or dispersion system can be prepared with low viscosities at high solids content; such coating systems containing 20-30% solids can readily be applied using conventional fluidized bed or pan-coating technology.

With the novel aqueous film coating system of the present invention the coating thickness and uniformity of coating of drugs can be more effectively controlled and the solid readily dispersible powdered form eliminates problems associated with shipping and shelf-stability of aqueous dispersions. The present coating system may contain a wide range of wax and lipid materials alone or in combination. Pigments, plasticizers, both water and water-insoluble polymers as well as drugs, may easily be incorporated into the present coating system.

DETAILED DESCRIPTION OF THE INVENTION

The present invention involves the emulsification of a lipid/wax mixture followed by spray drying to form a powder. The resultant powder is readily dispersible in water and may be coated on drug-containing granules, pellets, tablets and the like. The aqueous dispersions of waxes and lipids may be used for pharmaceutical coating applications of medicaments as, for instance, protective coatings, enteric coatings, sustained-release coatings and the like.

A typical formulation may include a lipid, i.e. partially hydrogenated cottonseed oil, an emulsifying agent, i.e., polysorbate, and/or a wax, i.e. castor wax. In carrying out the present invention the partially hydrogenated cottonseed oil may be heated in a water bath at 80°-85° C. A solution of polysorbate (Tween 65) heated to 90° C. is then added to the molten lipid mass with constant stirring. A dispersion of Veegum K in water heated to 90° C. is then added with stirring. The crude emulsion is then homogenized. An antifoam agent, for example, Antifoam AF, is added and made up to weight by adding hot distilled water. The emulsion is shock-cooled in an ice-bath with constant stirring. A smooth emulsion having a particle size between 1-5 microns is obtained.

The emulsion may then be applied to the coating of pellets, for example, by spray coating drug-coated nonpareil seeds in the coating vessel of a fluid-bed coating unit such as the Uni-Glatt in the usual manner. The spraying is carried out continuously until the desired increase in mean weight of drug-beads is achieved. The beads thus obtained have a smooth lustrous surface. If desired, suitable drug granulations may be coated with the described coating dispersion by spraying until the desired amount of lipid coat is applied.

With respect to the individual components of the lipid/wax composition of the present invention, the wax component is employed in an amount of from about 10% to about 30%, and preferably from about 15% to about 20%, by weight, of the total quantity of the emulsion. The lipid component, when employed, is employed in an amount of from about 10% to about 30%, and preferably from about 15% to about 20%, by weight, of the total quantity of the emulsion. The emulsifying agent is employed in an amount from about 0.5% to about 5%, and preferably from about 1% to about 3%, by weight, of the total quantity of the emulsion. Water is employed in an amount sufficient to balance the formulation.

The wax component of the emulsion may comprise any paraffin wax obtained from petroleum oil and may include microcrystalline wax such as obtained from petroleum residues; also, paraffin waxes modified with various polymers, e.g. polyethylene, or copolymers such as ethylene-vinyl acetate copolymers and similar polymeric materials may be included. In general, paraffin wax having a melting point of from about 115° F. to about 150° F. is preferred, and such wax may comprise high molecular weight hydrocarbons, comprising, generally, straight-chain compounds having a crystalline structure in solid form. Microcrystalline wax may be employed, as hereinbefore indicated, and is obtained from petroleum oil. This material may possess a melting point of about 150° F. to about 190° F. and contains a substantial portion of high molecular weight hydrocarbons having branched-chain and ring structures. This material is more plastic in nature than paraffin wax. Petrolatum is commercially obtained from petroleum and comprises a mixture of microcrystalline wax and petroleum oil.

Particularly useful waxes and lipids for use in the present invention include:

Carnauba Wax—melting point 79°-85° C.
Ceresin Wax—melting point 72°-75° C.
Microcrystalline Wax—melting point 70°-80° C.
Glyceryl Monostearate—melting point 60°-65° C.
Partially Hydrogenated Cottonseed Oil—melting point 62°-65° C.
Hydrogenated Castor Oil—melting point 85°-87° C. (Cutina HR/Castor Wax)

In addition to the foregoing waxes/lipids, the following have been successfully emulsified and spray dried. Hoechst Wax E, partially hydrogenated palm oil, Bees wax, Carnauba Wax and Bees Wax mixture, Cutina HR and Glyceryl Monostearate Mixture Hoechst wax, Bees wax and Paraffin wax mixture.

Surface active agents for use in the present invention may be of the anionic or nonionic type. The emulsifier employed in the wax/lipid emulsions of the present invention may be of the nonionic type and may also include emulsifiers of the anionic type in combination therewith. Many nonionic emulsifiers can be used in this emulsion provided the critical relationship between oil solubility and water solubility is maintained. Typical of such emulsifiers are mixtures of sorbitan monooleate and polyoxyethylene sorbitan monooleate. Typical other nonionic emulsifiers suitable for use in these wax/lipid emulsions are polyoxyethylene ethers of octyl or nonylphenol having variable amounts of ethylene oxide content per mole of finished product required to provide the oil and water solubility characteristics. Thus, for example, a portion of polyoxyethylene ethers of octyl phenol having about 5 moles of ethylene oxide per mole of finished product when blended with a like amount of polyoxyethylene ethers of octyl phenol having about 10 moles of ethylene oxide per mole of finished product, provides an emulsifier combination having the desired water and oil solubility. As the ethylene oxide content is reduced, oil solubility is enhanced, whereas as the ethylene oxide content is increased, water solubility is enhanced. A blended product having sufficient oil-soluble and water-soluble constituents and possessing an average ethylene oxide content per mole of finished product between about 5 and 10 is quite satisfactory. Other nonionic emulsifiers contemplated within the scope of the present emulsions are exemplified by partial esters of fatty acids (e.g. palmitic, stearic, oleic and the like) and hexitol anhydrides (hexitans and hexides) derived from sorbitol. These materials, to which polyoxyethylene chains have been added to the nonesterified hydroxyls to increase water solubility, are blended with the untreated material to ensure solubility balance. Also usable in this area are the condensation products of ethylene oxide and relatively high molecular weight polypropylene glycol. The molecular weight of the polypropylene glycol portion may be 1,000–2,000. The molecular weight of the compound may be as high as 8,000.

As emulsion stabilizing agents (co-emulsifiers) there may be mentioned the alcohols cetyl alcohol, stearyl alcohol, lauryl alcohol and the like. Acids such as stearic acid, lauric acid, palmitic acid, etc. may also be used as well as the hydrocolloids methyl cellulose and sodium carboxymethylcellulose. Such co-emulsifiers may be employed in amounts from 0% to 2% by weight. Suitable deflocculating agents such as sodium hexametaphosphate, sodium tetraphosphate, sodium tripolyphosphate and potassium metaphosphate may advantageously be used in the present composition in amounts from about 0% to about 1% by weight.

The invention will be described in greater detail in conjunction with the following specific examples in which the parts are by weight unless otherwise specified.

EXAMPLE 1

| PREPARATION OF EMULSION: | | |
| --- | --- | --- |
| Ingredients | | Grams |
| Partially Hydrogenated Cottonseed Oil | | 250 |
| Polysorbate 65 (Tween 65) | | 15 |
| Veegum K | | 10 |
| Antifoam AF (Semithicon Emulsion) | | 10 |
| Distilled Water | q.s. | 1000 |

250 g of partially hydrogenated cottonseed oil is heated in a water bath at 80°-85° C. A 10% solution of Tween 65, heated to 90° C., is then added to the molten lipid mass with constant stirring using a suitable lab mixer such as a Brookfield counter rotating mixer. A 4% dispersion of Veegum K in water heated to 90° C. is then added with stirring. The crude emulsion is then homogenized using a homomixer or other suitable homogenizer. The Antifoam AF is added and made up to weight by adding hot distilled water. The emulsion is shock-cooled in an ice-bath with constant stirring. A smooth emulsion having a particle size between 1-5 micron is obtained.

COATING OF PELLETS 600 g of drug-coated non-pareil seeds are placed in the coating vessel of a fluid-bed coating unit such as the Uni-Glatt. The drug beads are sprayed with the coating emulsion of the above-described composition according to the usual method. The bed temperature is closely monitored and is kept 3°-5° C. lower than melting point of the lipid. The spraying is carried out continuously until the desired increase in mean weight of drug-beads is achieved. The beads thus obtained have a smooth and lustrous surface.

EXAMPLE 2

SPRAYING DRYING OF EMULSION

The coating emulsion of the composition described in Example 1 is spray dried in a laboratory size spray dryer. The drying conditions selected are such that the spray drying chamber temperature is maintained at least 5° C. below the melting point of the wax. A free-flowing powder is obtained with an average particle size of 1-5 micron.

PREPARATION OF COATING DISPERSION 200 g of the above-described spray dried powder is dispersed in sufficient distilled water to give 500 g of final dispersion. A suitable lab mixer such as a Brookfield mixer or Waring blender is used to ensure complete dispersion of the spray dried powder in the aqueous media.

COATING OF GRANULATION 500 g of drug granulation are placed in the coating vessel of a Uni-Glatt coater. The above-described coating dispersion is sprayed continuously until the desired amount of lipid coat is applied.

EXAMPLE 3

| Spray Dried Lipid Emulsion | 200 g |
|---|---|
| Talc | 40 g |
| Citroflex-4 | 40 g |
| Distilled Water | q.s. 700 g |

The spray dried lipid emulsion, talc and citroflex-4 are dispersed in distilled water with the help of a suitable lab mixer. The resulting dispersion is passed through a homogenizer to ensure completeness of dispersion. Drug-beads are coated in a fluid bed coating unit as described in Example 1.

What is claimed is:

1. A process for spray-coating medicaments or foods which comprises spraying onto the surface of the medicament an aqueous dispersion of a powder, said powder having been formed by spray drying an emulsion to consisting essentially of a member selected from the group wax, lipid and a mixture thereof, an emulsifying agent and water.

2. The process according to claim 1 wherein the member is partially hydrogenated cottonseed oil.

3. The process according to claim 1 wherein the wax is carnuba wax.

4. The process according to claim 1 wherein the wax is castor wax/cutina HR.

5. The process according to claim 1 wherein the wax is Hoechst wax E.

6. The process according to claim 1 wherein the wax is paraffin wax.

7. The process according to claim 1 wherein the wax is bees wax.

8. The process according to claim 1 wherein the wax is bees wax.

9. The process according to claim 1 wherein the wax is a mixture of carnuba wax and bees wax.

10. The process according to claim 1 wherein the wax is mixture of Hoechst wax E, bees wax and paraffin wax.

11. The process according to claim 1 wherein the lipid is glyceryl monostearate.

12. The process according to claim 1 wherein the member is a mixture of castor wax and glyceryl monostearate.

* * * * *